(12) United States Patent
Mönkmeyer

(10) Patent No.: US 8,406,908 B2
(45) Date of Patent: Mar. 26, 2013

(54) METHOD AND SYSTEM FOR PRODUCING A DENTAL PROSTHESIS

(76) Inventor: Ulrich Mönkmeyer, Cala d'Or (ES)

( * ) Notice: Subject to any disclaimer, the term of this patent is extended or adjusted under 35 U.S.C. 154(b) by 284 days.

(21) Appl. No.: 12/441,500

(22) PCT Filed: Sep. 14, 2007

(86) PCT No.: PCT/EP2007/008031
§ 371 (c)(1),
(2), (4) Date: Nov. 12, 2009

(87) PCT Pub. No.: WO2008/031614
PCT Pub. Date: Mar. 20, 2008

(65) Prior Publication Data
US 2010/0049351 A1    Feb. 25, 2010

(30) Foreign Application Priority Data
Sep. 14, 2006  (DE) .......................... 10 2006 043 284

(51) Int. Cl.
*G06F 19/00* (2011.01)
(52) U.S. Cl. ........................................ 700/98; 433/72
(58) Field of Classification Search .................. 700/95, 700/98; 433/72
See application file for complete search history.

(56) References Cited

U.S. PATENT DOCUMENTS

| | | | | |
|---|---|---|---|---|
| 4,742,464 | A * | 5/1988 | Duret et al. | 700/183 |
| 6,679,700 | B2 * | 1/2004 | McGann | 433/24 |
| 7,442,040 | B2 * | 10/2008 | Kuo | 433/202.1 |
| 7,600,999 | B2 * | 10/2009 | Knopp | 433/24 |
| 7,658,610 | B2 * | 2/2010 | Knopp | 433/24 |
| 2004/0219476 | A1 * | 11/2004 | Dadi | 433/72 |
| 2004/0229185 | A1 * | 11/2004 | Knopp | 433/24 |
| 2004/0253562 | A1 * | 12/2004 | Knopp | 433/24 |
| 2005/0042569 | A1 * | 2/2005 | Phan et al. | 433/24 |
| 2005/0064360 | A1 * | 3/2005 | Wen et al. | 433/24 |
| 2005/0089822 | A1 * | 4/2005 | Geng | 433/215 |
| 2006/0019219 | A1 * | 1/2006 | Saliger et al. | 433/173 |
| 2006/0084030 | A1 * | 4/2006 | Phan et al. | 433/72 |
| 2006/0154207 | A1 * | 7/2006 | Kuo | 433/202.1 |
| 2006/0257817 | A1 * | 11/2006 | Shelton | 433/75 |
| 2007/0009855 | A1 * | 1/2007 | Stonisch | 433/215 |
| 2008/0064005 | A1 * | 3/2008 | Meitner | 433/74 |
| 2008/0096152 | A1 * | 4/2008 | Cheang | 433/24 |

(Continued)

FOREIGN PATENT DOCUMENTS

DE     10 2005 034 803 A1    3/2006

*Primary Examiner* — Mohammad Ali
*Assistant Examiner* — Anthony Whittington
(74) *Attorney, Agent, or Firm* — Patterson Thuente Pedersen, P.A.

(57) ABSTRACT

A method for producing a dental prosthesis, including obtaining data for the teeth that are to be replaced and for their surrounding area; compiling a database containing data for prefabricated tooth replacement parts; excluding those tooth replacement parts which, based on the data recorded for the teeth to be replaced and for their surrounding area, are unsuitable for functional and/or aesthetic and/or stability reasons; selecting the tooth replacement parts to be used; using imaging software to obtain a virtual representation of the tooth replacement parts integrated into the surrounding area in the patient's dentition in accordance with customary set-up rules; recording the data of an actual situation in a patient's mouth after preparation of the affected teeth and insertion of any implants; checking the compliance of the selected tooth replacement parts with the data of the actual situation after preparation; making available the selected tooth replacement parts; modifying the selected tooth replacement parts according to the data of the actual situation after preparation.

12 Claims, 9 Drawing Sheets

U.S. PATENT DOCUMENTS

| | | | |
|---|---|---|---|
| 2008/0160485 A1* | 7/2008 | Touchstone | 433/215 |
| 2008/0166681 A1* | 7/2008 | Weinstein et al. | 433/76 |
| 2008/0176189 A1* | 7/2008 | Stonisch | 433/215 |
| 2010/0159412 A1* | 6/2010 | Moss et al. | 433/24 |
| 2010/0159413 A1* | 6/2010 | Kuo | 433/24 |

* cited by examiner

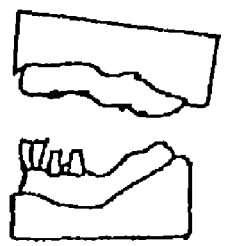
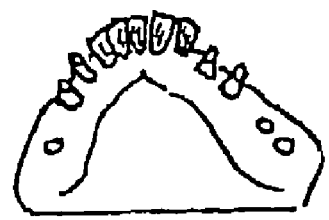
FIG. 2a                FIG. 2b
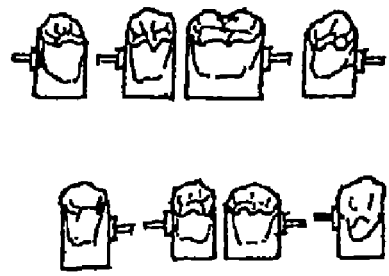
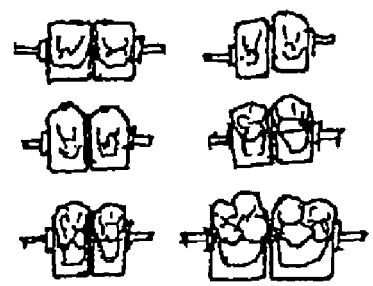
FIG. 3a                FIG. 3b
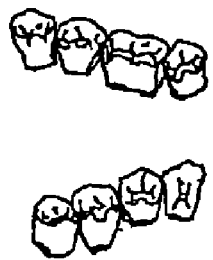
FIG. 4a                FIG. 4b

FIG. 5a  FIG. 5b
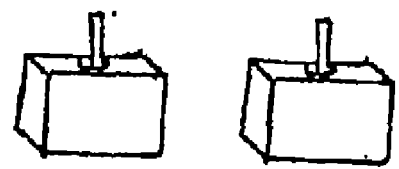
FIG. 5c  FIG. 5d
FIG. 5e  FIG. 5f

METHOD AND SYSTEM FOR PRODUCING A DENTAL PROSTHESIS

RELATED APPLICATIONS

The present application is a national stage entry of PCT Application No. PCT/EP2007/008031, filed Sep. 14, 2007, which claims priority from German Application No. 10 2006 043 284.3, filed Sep. 14, 2006, the disclosures of which are hereby incorporated by reference in their entireties.

FIELD OF THE INVENTION

The invention relates to a method as well as a system for producing a dental prosthesis.

BACKGROUND OF THE INVENTION

A dental prosthesis—be it crowns, bridges, a partial prosthesis or a total prosthesis—consists of an outer shell and a marginal part, which usually consists of a framework. The outer shell must satisfy aesthetic requirements and, depending on the tooth, allow for functionally suitable articulation. The marginal part must be designed in such a way that the prosthesis can be anchored securely in the mouth of the patient—permanently or removably.

Conventional dental prostheses are individually made by hand. Design and fabrication are carried out from the prepared tooth outward to the outer shell, which is completed only after the marginal part with one or more frameworks has been constructed.

Patients who require a dental prosthesis go through the following phases: Anamnesis is followed by the examination, followed by diagnosis and the selection of a therapy. Afterwards, the actual treatment commences with the hygiene phase and pre-prosthetic preliminary treatment. After completion of said preliminary treatment, the prosthetic work can commence with planning and fabrication of the special crowns or bridges, the partial or total prosthetic care.

For the realization of crown or bridge tooth replacement, it is common today to carry out a test preparation on the gypsum model before the preparation on the patient and after the casting and construction of the model. Depending on the form in which the fabrication of temporary replacements is planned, an alginate or silicone casting, a deep-drawn foil or a temporary shell model must be constructed before the grinding of the tooth, which is to be replaced. Furthermore, it is recommended to select the color prior to the preparation.

During preparation, several issues have to be considered: protection of the pulp, protection of the marginal paradontium as well as obtainment of a retention and resistance form, taking into account materials-technological, construction-related, and aesthetic factors.

Preparation and cleaning of the ground tooth remnant is followed by the definitive casting. A model is subsequently produced in the lab. In case of a combination of fixed and removable tooth replacement, e.g., the following method is applied:

At first, the preparation model and the inner crowns are produced. At the clinic, the fitting of the inner crowns (primary crowns) and the fixation casting are carried out. In the next step, the construction model and jaw relation record are fabricated in the lab. Facial arc transfer, jaw relation determination, and model assembly are, once again, carried out at the clinic. Now, the tooth set-up in wax is prepared at the lab and subsequently fitted at the clinic. In the next step, the outer crowns (secondary crowns) and the connecting framework (tertiary structure) are fabricated. The design and processing of the frameworks mainly adheres to aesthetic aspects; therefore, the framework is produced as delicately as possible, even at the expense of its service life. In practice, a sufficient dimensioning of the frameworks cannot be controlled with complete accuracy.

The build-up of the ceramic masses onto the metal framework—the thermal expansion coefficients of which must be matched—is carried out through mixing of ceramic powder with distilled water and application of the resulting sludge with a brush onto the areas to be encrusted. The ceramic masses are layered in portions next to and/or on top of each other. The resulting form, which varies with the skill of the individual dental technician, is subsequently sintered in the ceramic kiln at the appropriate temperature. The results are not identically reproducible, particularly for structures which include several teeth.

Now, the connecting framework together with the definitive tooth set-up in wax is fitted once again at the clinic.

During the same sitting, a possible aesthetic processing can also be carried out. The functional and aesthetic shell of the tooth replacement emerges during the last step of the process and is not—or only in a very limited fashion—foreseeable during the planning phase. Subsequently, the surfaces are mechanically polished. Finally, the tooth replacement is integrated according to known methods.

The disadvantage of the methods used to this date relates to the construction of the tooth replacement from the inside out, i.e., the outer aesthetic shell is determined only during the last step. Patient, dentist, and dental technician have no or only a vague idea how the finished tooth replacement will look since the result essentially depends on the manual skills of the dental technician.

Particularly, the patient cannot reach any sound joint decision when questions regarding aesthetics versus stability and function are to be assessed. Furthermore, the known method consists of many individual steps to be executed successively, and the patient has to live with a temporary replacement and many fittings for a long time.

SUMMARY OF THE INVENTION

Embodiments of the invention provide a method which allows for the quick fabrication of dental prostheses with predictable results. Furthermore, embodiments of the invention propose to create a system which facilitates the execution of said method.

At first, the task is solved with a method for producing a dental prosthesis, which includes the following steps:
  obtaining data for the teeth that are to be replaced and for their surrounding areas;
  compiling a database containing data for prefabricated tooth replacement parts;
  excluding those tooth replacement parts which, based on the data recorded for the teeth to be replaced and for their surrounding area, are unsuitable for functional and/or aesthetic and/or stability reasons;
  selecting the tooth replacement parts to be used;
  using imaging software to obtain a virtual representation of the tooth replacement parts integrated into the surrounding area in the patient's dentition in accordance with customary set-up rules;
  recording data of an actual situation in a patient's mouth after preparation of the affected teeth and insertion of any implants;

checking the compliance of the selected tooth replacement parts with the data of the actual situation after preparation;

making available the selected tooth replacement parts;

modifying the selected tooth replacement parts according to the data of the actual situation after preparation.

According to the method, the data of the teeth to be replaced as well as their surrounding areas are also obtained. This includes all teeth, which are affected by the dental prosthesis to be produced, e.g., also anchor teeth for a bridge. The recording can be carried out by customary methods, e.g., by means of a model. The surrounding area consists, among others, of the facial morphology and the facial frame derived from said facial morphology, and significantly determines the selection and set-up of the teeth. E.g., in Claude Rufenacht's *Principles of Aesthetic Integration*, Quintessenz, Berlin 2000, incorporated herein by reference in its entirety, those interdependencies are presented in detail. In the facial composition, e.g, the vertical median line, which crosses the line of occlusion, is a constant, regardless of the various ethnic features and individual differences. From the ratio of the total facial frame, which corresponds with the extent of the bone structure, and the vestibular frame around the receptor's eyes, nose, and mouth, an age-related set-up of the teeth can be determined.

The tooth replacement to be used is then chosen from a selection of prefabricated tooth replacement parts. Data of prefabricated tooth replacement parts is compiled in a database.

Such tooth replacement parts can be, e.g., customarily manufactured and commercially available, polychromatic sets of teeth. However, the use of tooth replacement parts, which solely consist of enamel-imitating materials (plastic, ceramic, or other suitable materials) is also possible.

In the next step, tooth replacement parts are excluded from the database, which, based on the recorded data of the actual situation, are geometrically unsuitable. These are, e.g., teeth which are too big or too small.

The data required for such purpose is obtained during the recording of the surrounding area. This, e.g., can be carried out by means of image recognition systems. With the additional aid of recognized rules, it can be ascertained, which of the tooth replacement parts in the database can and cannot be set up in accordance with said rules. The latter can be excluded. However, the exact content of such rules is irrelevant for the execution of embodiments of the invention. Any rule, which correlates the data of the surrounding area and the tooth replacement parts, shall suffice hereto.

Now the tooth replacement parts to be used are selected from the tooth replacement parts which are not excluded in the database. Since the outer shells of the tooth replacement parts, which remain in the database after exclusion of the unsuitable tooth replacement parts, are all suitable with regard to technical aspects, and which were preselected in accordance with the rules contained in the database, any arbitrary combination can, in principle, be used. A fully automatic selection can be made.

Subsequently, the selected tooth replacement parts are virtually integrated in the dentition of the patient in accordance with customary set-up rules and represented in the surrounding area, based on the recorded data and with the use of imaging software. During this phase, the patient can already recognize what the selected tooth replacement will look like after completion and integration. If the patient is not satisfied with the result, a different combination of tooth replacement parts can be chosen and the result represented.

Optionally, the outer shell of the selected tooth replacement parts can also be processed virtually until an aesthetically acceptable result is achieved. In addition, the set-up of the selected tooth replacement parts can optionally be modified.

According to the method, the data of an actual situation in the mouth of a patient is recorded after preparation of the affected teeth and insertion of possible implants. Once again, this is achieved in accordance with customary methods and, if necessary, also with the use of a model.

In the next step, compliance of the selected tooth replacement parts with the data of the actual situation after preparation is checked. In this step, it is verified whether the selected tooth replacement parts can be processed in such a way that they can be used for the existing actual situation after preparation. If the data is consistent, the selected tooth replacement parts are made available. Then the tooth replacement parts are modified according to the data of the actual situation after preparation.

The tooth replacement parts can be processed and/or provided with conventional support structures, such as frameworks.

Therefore, during the compliance check in the previous step it is also verified whether the remaining material thickness suffices and/or whether there is sufficient space for the necessary framework once the required processing is carried out in view of the actual situation at hand. The technical requirements regarding minimum layer strengths, bonding strengths, and configuration can be found, e.g., in the materials-specific ISO standards and are hereby included.

In the event that the marginal measurements of the selected tooth replacement parts cannot be brought in line with the completed preparation, the method must be repeated from the step regarding the selection of the tooth replacement parts to be used. Alternatively, the preparation can also be reworked and the method repeated merely from the step regarding the recording of the actual situation after preparation.

According to embodiments of the invention, the fabrication of the tooth replacement is not carried out, as is customary in prior art, from the inside out, i.e., from the prepared tooth to the outer shell, but proceeds from the outer shell to the fitting onto the prepared tooth. Therefore, the tooth replacement can be fabricated from prefabricated sets of teeth by following the modular design. Since the outer shell of the tooth is determined in the first step, the result to be achieved can be quickly visualized and evaluated. For the first time, the patient has the opportunity to see in advance his/her appearance after execution of the treatment. Furthermore, a temporary replacement for the patient, made of plastic, can be generated inexpensively from the recorded data.

If, depending on the tooth replacement to be fabricated, additional components are required, e.g., framework structures for bridges, such components can also be taken into consideration within the course of the compliance check.

If the tooth replacement parts consist exclusively of enamel-imitating materials, the necessary framework shall imitate for its outer design the shape and structure of the natural dentine build-up.

Optionally, the mathematically determined data can be saved for such elements. As a result, all components of the tooth replacement can subsequently be fabricated immediately. This guarantees that the frameworks responsible for the stability and service life of the tooth replacement are not arbitrarily produced manually but in accordance with objective specifications. Furthermore, the patient can already evaluate the aesthetic impact of the selected tooth replacement during the planning phase.

The selected tooth replacement parts can be modified with the use of the CAD method.

If no compliance between the selected tooth replacement parts and the data of the actual situation after preparation is determined during the step regarding the compliance check, modifications for achieving compliance can be proposed, such as additional preparations of the teeth, a different set-up, and others.

The order of the aforementioned procedural steps—aside from mandatorily sequential steps—is freely selectable.

According to embodiments of the invention, a system for producing tooth replacement includes the following elements:

means for recording data of the teeth to be replaced as well as their surrounding areas;

a database with data of prefabricated tooth replacement parts;

means for excluding those tooth replacement parts from the database which, based on the data recorded for the teeth to be replaced or for their surrounding area, are unsuitable for functional and/or aesthetic and/or stability reasons;

means for selecting the tooth replacement parts among those tooth replacement parts which remain in the database;

means for a virtual representation of the selected tooth replacement parts integrated into the surrounding area in the patient's dentition in accordance with customary set-up rules;

means for recording the data of an actual situation in a patient's mouth or with the use of a model after preparation of the affected teeth and insertion of any implants;

means for checking the compliance of the selected tooth replacement parts with the data of the actual situation after preparation;

means for modifying the selected tooth replacement parts according to the data of the actual situation after preparation.

With such a system, the method described above can be executed.

The system includes a database, in which the data for the prefabricated tooth replacement parts is stored.

The system includes means for recording the data of the teeth to be replaced and their surrounding areas as well as a virtual representation of the tooth replacement parts integrated into the surrounding area in the patient's dentition in accordance with customary set-up rules.

Furthermore, the system includes means for excluding those tooth replacement parts from the database which, based on the data recorded for the surrounding area, are unsuitable for functional and/or aesthetic and/or stability reasons.

For the selection of tooth replacement parts from the database, respective means are also provided.

The system also provides for respective means for recording the actual situation in a patient's mouth after preparation of the affected teeth and insertion of any implants as well as means for checking the compliance of the selected tooth replacement parts with the data of the actual situation after preparation. With applicable matching algorithms it can be determined whether the selected tooth replacement parts, with regard to their marginal part, can be adapted to the situation after preparation. If this is not possible with the use of customary criteria, e.g., stability, optional means can be provided, which represent the required adjustment, e.g., additional preparation, modified set-up, or alternative materials.

BRIEF DESCRIPTION OF THE DRAWINGS

An embodiment of the method, according to the invention, the systems are shown by means of an example case with reference to the attached illustrations:

FIGS. 2a and 2b depict jaw-relation model according to an embodiment of the invention;

FIGS. 3a-4b depict outer forms suggested by the system for fabrication of a temporary replacement, according to an embodiment of the invention;

FIG. 5a depicts a ready-made abutment according to an embodiment of the invention;

FIG. 5b depicts a cross-section of a lower jaw model with individualized abutments according to an embodiment of the invention;

FIGS. 5c-5f depict tooth replacement parts fabricated for the lower jaw according to an embodiment of the invention;

FIG. 7a is a right lateral view of the entire tooth replacement according to an embodiment of the invention;

FIG. 7b is a frontal view of the entire tooth replacement of FIG. 7a;

FIG. 7c is a left lateral view of the entire tooth replacement of FIG. 7a;

FIG. 9b depicts a framework structure of the prefabricated tooth replacement parts of FIG. 9a.

DETAILED DESCRIPTION OF THE DRAWINGS

Figure 1A:
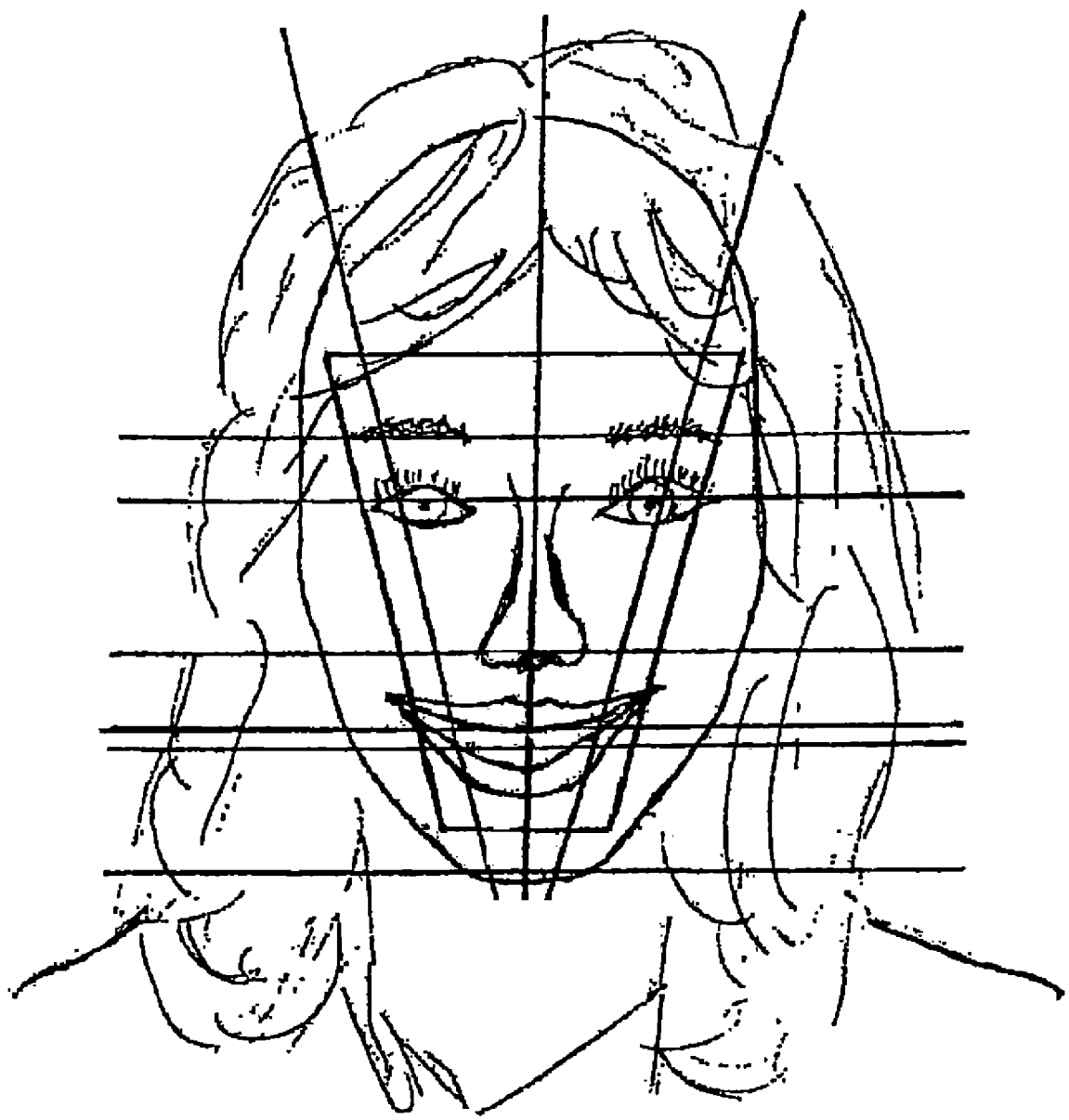
FIGS. 1a-1d depict virtual representations of a surrounding are of affected teeth, according to an embodiment of the invention.
Figure 1B:
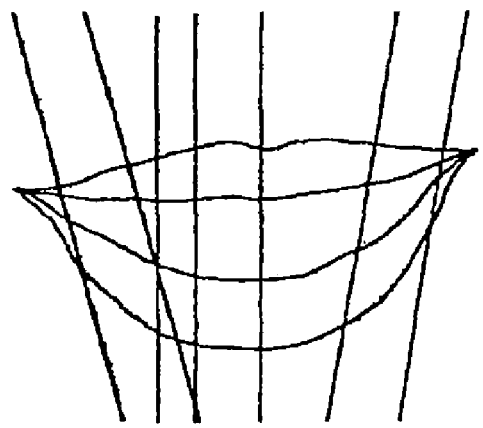
Figure 1C:
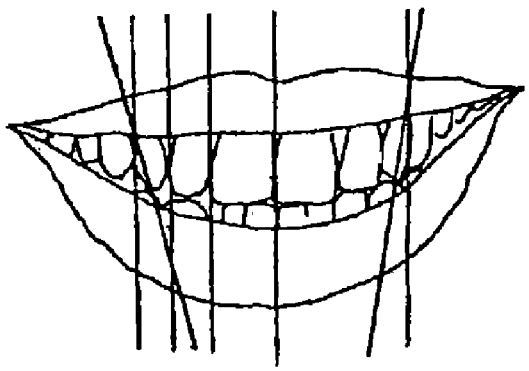
Figure 1D:
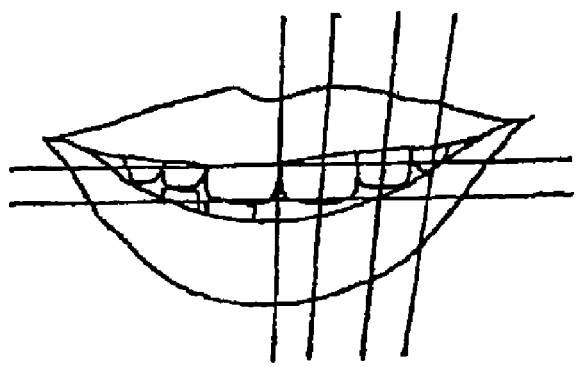

The initial findings of the 40-year old female patient showed multiple tooth-decay and paradontosis-related defects, which had also caused significant vertical and horizontal hard tissue deficits.

The patient requested an implant-supported tooth replacement without metal.

The goal of the preliminary treatment was to let the tissue heal in order to allow for extensive surgical measures (autologous iliac crest grafts, soft tissue conditioning, and finally, insertion of the situationally possible implants).

In order to record the data for the affected teeth and their surrounding areas, the horizontal and vertical jaw relation was determined by means of a jaw relation record and coded in such a way that it was reproducible. The data of the actual situation of the affected teeth was scanned from models of the patient.

From a database, which contained the available data regarding prefabricated tooth replacement parts, the system suggested the tooth replacement parts, which were suited for possible use, while excluding the unsuitable tooth replacement parts, and generated a set-up suggestion. The recorded data of the surrounding area was taken into consideration, the facial aesthetic and functional factors, e.g., according to the rules by Rufenacht, were determined, and the set-up suggested accordingly.

With an imaging system, the patient was digitally photographed from the front and bilaterally. With the data stored in the system, the line of occlusion as well as the commissure line were determined. By means of the lateral images, the respective planes were generated. The relevant vertical lines were also generated (median line, line on which the axial position of the canines must be arranged).

With the help of the imaging system it was possible to picture the suggested result in the visible area.

The set-up suggestion was varied in coordination with the patient. E.g., an intraoral check of the proportions and alignment of the teeth relative to the lip line, the smile line, and the profile, was performed.

At this point, the aesthetic result (the outer shell of the tooth replacement) was virtually visible and largely predictable.

After casting and fabrication of the master models, they were articulated, according to the jaw relation determination, and also scanned.

Based on this data, the temporary replacement was produced, which also represented the outer shell of the future tooth replacement. The inserted temporary replacement already showed in its outer shape and color the final result.

During the check regarding compliance of the selected all-ceramic tooth replacement parts with the data of the actual situation after preparation, it turned out that planning with metal-free all-ceramic frameworks in the lower jaw was not possible for stability reasons. Therefore, a metal framework was designed, which was based on the measured insufficient free space, and which guaranteed sufficient stability at a small height. After said modification, the respective tooth replacement parts were replaced.

Said modification as well as its necessity was demonstrated to the patient and her approval for the alteration in the planning obtained. This possible source of error was already eliminated before the fabrication of the frameworks. As a result, a subjective, manual, reducing alteration and resulting weakening of the framework design was avoided.

Since all relevant data had been recorded at this time, the system was able to calculate the design of the required tooth replacement parts. With said data, the connecting bars, the mesio-structures, the secondary structure as well as the inner surface fit of the selected prefabricated plastic tooth were manufactured at the same time on various milling, grinding, and/or galvanizing machines.

FIG. 1a to 1d clarify that the various aspects of the surrounding area of the affected teeth must be taken into consideration statically and dynamically during the aesthetic analysis, and which results in the rules for the set-up of the teeth.

In the facial composition, the vertical median line, which crosses the line of occlusion, is a constant, regardless of the various ethnic features and individual differences.

From the ratio of the total facial frame, which corresponds with the extent of the bone structure, and the vestibular frame around the receptors eyes, nose, and mouth, an age-related set-up of the teeth can be determined. The virtual stylizing to geometric figures, required by the system, is used for determining optimal facial proportions. The program used for such purpose takes advantage of the fact that the facial receptors are located parallel to the upper and lower edge of the vestibular frame. It furthermore applies the fact that a line drawn from the outer edge of the eye to the outer edge of the lip runs parallel to the outer vertical boundary line. Since the upper line of occlusion also runs parallel to the horizontal boundary lines of the vestibular frame and the commissure line, the program can determine the lower line of occlusion, which is visible with the mouth open. Vertically, the axial direction of the canine can be derived from the parallelism to the vertical lines of the facial frame. Based on the aforementioned, and in accordance with the rules of the golden section, the division of the areas for the lateral and central incisors can be determined.

The system provides a virtual representation of the resulting method-dependent set-up since the program contains and has the ability to use the rules described in various publications (see, e.g., Claude Rufenacht's *Principles of Aesthetic Integration*, Quintessenz, Berlin 2000). Said representation can be discussed with the patient and navigated within the system-dependent database for tooth replacement parts. The desired result of the tooth replacement, its aesthetic and functional outer shell, can now be predicted.

FIGS. 2a and 2b show how the models and their relations to each other are scanned and correlated with the previously obtained patient data after the jaw relation determination and fabrication of the models as well as the jaw-relation appropriate orientation of the models, e.g., in an articulator or also virtually in accordance with an appropriate program or method.

As shown in FIGS. 3a, 4a, 3b, and 4b, the outer forms suggested by the system for the fabrication of a temporary replacement are retrieved from respective physical storage; in a CNN machine, which contains and uses the data of the contours of the tooth and/or implant structures at hand, the inner fit for said outer forms through milling and/or grinding of the lumen is produced. The data of the variations made for the outer areas are used to generate the outer areas as well as produce the outer fit through milling and/or grinding down to the preparation limits. The temporary replacement can be integrated. It corresponds with the result compiled in step 1.

Since the absolute measurements for the tooth replacement result from the free space of the upper and lower jaw models orientated to each other, and since the outer shell is already established, the bearing structures (frameworks) can be constructed. The minimum thickness with regard to the individual possible materials are stored in the system according to the data resulting from ISO standards. Therefore, the materials to be used in this step of the method can still be varied. FIG. 2a shows insufficient space for a ceramic framework in the posterior area between upper jaw implant regio 6 and lower jaw implant regio 6. Respectively, the system suggests a different solution. A framework, in this case made of titanium, (FIGS. 5c and d) requires far less height and is therefore suitable. The patient must compromise and accept a solution which is not completely free of metal.

FIG. 5a shows the ready-made abutment, FIG. 5b shows the lower jaw model with the individualized abutments as cross-section seen lingually, right lateral and left lateral. FIG. 5c to 5f show the tooth replacement parts which are fabricated for the lower jaw.

The prefabricated polychromatic outer crowns in FIG. 5e resemble in their outer shape those for temporary replacement. The inner contour of the outer crown takes into consideration their material-dependent minimum wall thickness as well as the geometry of the framework structures (FIG. 5d).

Figure 6A:
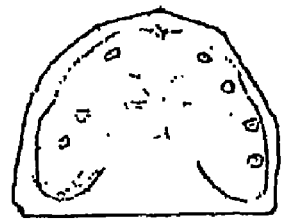
FIG. 6a is a representation of an upper jaw according to an embodiment of the invention.
Figure 6B:
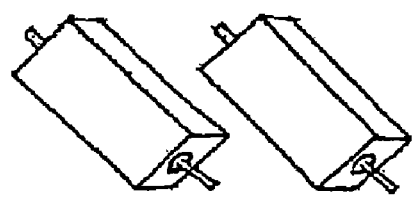
FIG. 6b depicts zirconium oxide blocks from which implants are milled according to an embodiment of the invention.
Figure 6C:
FIG. 6c depicts zirconium oxide primary structures milled from the zirconium oxide blocks of FIG. 6b.

Since the upper jaw (FIG. 6a) can only be provided with a removable tooth replacement, a more elaborate framework structure must be chosen. FIG. 6c shows the zirconium oxide primary structures, which are screwed onto the implants in the mouth and which are milled from zirconium oxide blocks (FIG. 6b).

Figure 6D:
FIG. 6d depicts a mesio-structure according to an embodiment of the invention.
Figure 6E:
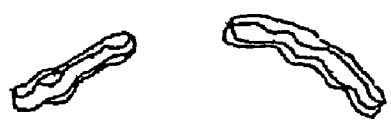
FIG. 6e depicts the fit of the mesio-structure of FIG. 6d.

A mesio-structure, which guarantees the hold of the removable part on the tightly screwed part, is galvanically produced from pure gold with a defined thickness (FIG. 6d). After a brief manual fitting onto the primary framework, a perfect fit is predictable (FIG. 6e).

Figure 6F:
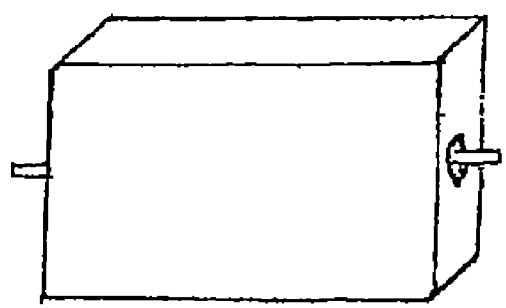
FIG. 6f depicts a zirconium oxide block from which implants are milled according to an embodiment of the invention.
Figure 6G:
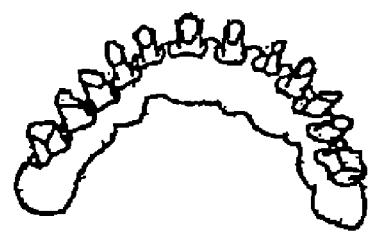
FIG. 6g depicts a second structure milled from the zirconium oxide block of FIG. 6f.
Figure 6H:
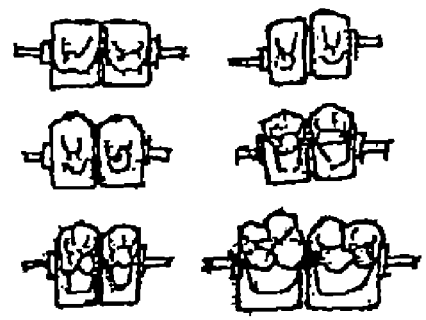
FIG. 6h depicts tooth replacement parts fabricated for the upper jaw according to an embodiment of the invention.
Figure 6I:
FIG. 6i depicts the fit of the prefabricated outer crowns of FIG. 6h.

Simultaneously, the secondary structure is produced from zirconium oxide on another CNN machine (FIG. 6f). The prefabricated outer crowns in FIG. 6i resemble in their out shape, analogously to the lower jaw replacement, those for temporary replacement. The inner contour takes into consideration their material-dependent minimum wall thickness as well as the cumulated measurements of the framework structures (primary, mesio, and secondary part).

Figures 7A, 7B, 7C:
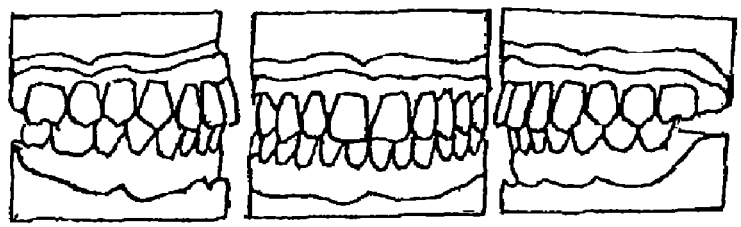

FIG. 7a to 7c show the entire tooth replacement after assembly of the individual parts on the models, right lateral, frontal, left lateral.

Figure 8A:
FIGS. 8a and 8b depict an integrated tooth replacement according to an embodiment of the invention.
Figure 8B:
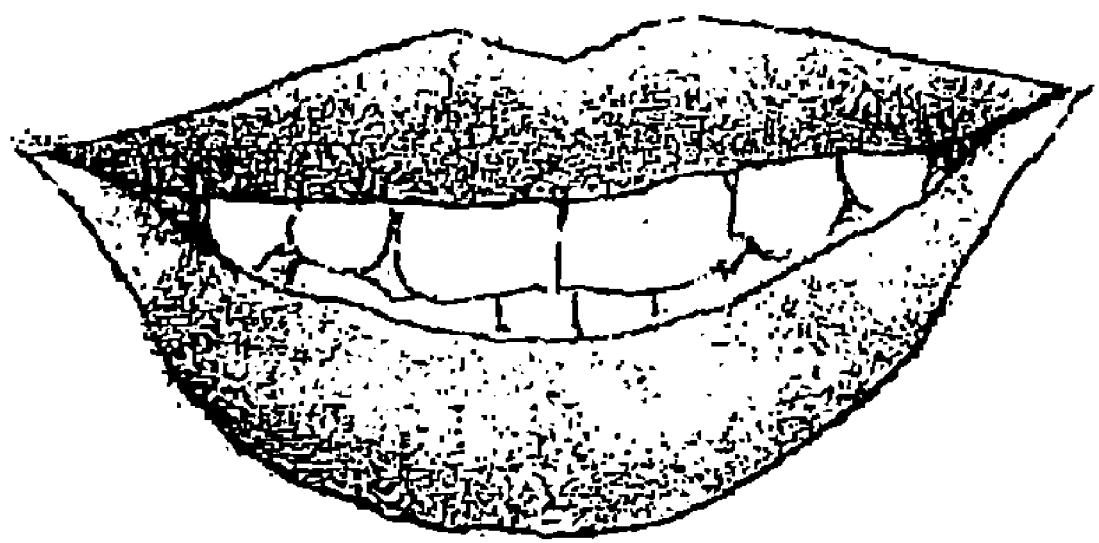

The integrated tooth replacement (FIGS. 8a and 8b) in the patient shows no surprises—it resembles the preview planned and documented in step 1 as well as the temporary replacement, which the patient has worn intermittently.

Figure 9A:
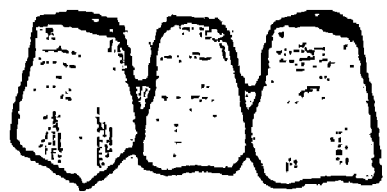
FIG. 9a depicts prefabricated tooth replacement parts consisting of enamel-imitating material according to an alternative embodiment of the invention.
Figure 9B:
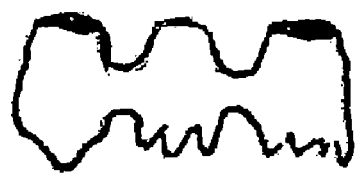
Figure 9C:
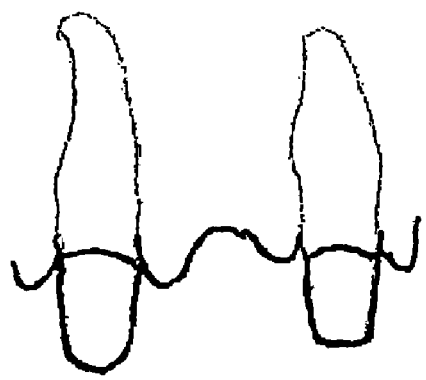
FIG. 9c depicts the bridge of FIG. 9a attached to prepared tooth remnants.

Alternatively, the prefabricated tooth replacement parts can consist exclusively of enamel-imitating material (FIG. 9a). In such cases, the framework structure imitates the structure and form of the tooth dentine (FIG. 9b). Together, this results once again in a complement of outer shape (outer shell) and supporting structure (in this case with the outer shape of the imitated natural dentine build-up). Once connected, the bridge can now be attached to the prepared tooth remnants (FIG. 9c).

The invention claimed is:

1. A method for producing a dental prosthesis the method comprising:
   obtaining data for the teeth that are to be replaced and for surrounding areas of the teeth of a patient;
   compiling a database containing data for prefabricated tooth replacement parts, the tooth replacement parts prefabricated prior to being selected for use with a specific patient to have an outer surface at least partially shaped to have the appearance of a tooth and further having an inner surface that is machined for the specific patient;
   excluding tooth replacement parts from the database which, based on the data recorded for the teeth to be replaced and for their surrounding area, are unsuitable for at least one of functional, aesthetic, and stability reasons;
   selecting tooth replacement parts from the database to be used;
   using imaging software to obtain a virtual representation of the tooth replacement parts integrated into the surrounding area in dentition of the patient in accordance with customary set-up rules;
   recording data of an actual situation in a mouth of the patient after preparation of the affected teeth and insertion of any tooth replacement parts;
   checking compliance of the selected tooth replacement parts with the data of the actual situation after preparation;
   making available the selected tooth replacement parts; and
   modifying the selected tooth replacement parts according to the data of the actual situation after preparation.

2. The method, according to claim 1, wherein at least one of the tooth replacement parts and the set-up are modified in a virtual representation in the surrounding area.

3. The method, according to claim 1, wherein the selected tooth replacement parts are modified with use of a CAD method.

4. The method, according to claim 1, further comprising: providing suggestions for alterations to achieve compliance if no compliance between the selected tooth replacement parts and the data of the actual situation after preparation is determined.

5. A system for producing a dental prosthesis, the system comprising:
   means for recording data of teeth to be replaced as well as surrounding areas of the teeth of a patient;
   a database containing data of prefabricated tooth replacement parts, the tooth replacement parts prefabricated prior to being selected for use with a specific patient to have an outer surface at least partially shaped to have the appearance of a tooth and further having an inner surface that is machined for the specific patient;
   means for excluding tooth replacement parts from the database which, based on data recorded for the teeth to be replaced and for their surrounding area, are unsuitable for at least one of functional, and aesthetic, and stability reasons;
   means for selecting tooth replacement parts among the tooth replacement parts which remain in the database;
   means for providing a virtual representation of the selected tooth replacement parts integrated into the surrounding area in the dentition of the patient in accordance with customary set-up rules;
   means for recording data of an actual situation in a mouth of the patient or with use of a model after preparation of the affected teeth and insertion of any tooth replacement parts;
   means for checking the compliance of the selected tooth replacement parts with the data of the actual situation after preparation; and
   means for modifying the selected tooth replacement parts according to the data of the actual situation after preparation.

6. The system according to claim 5, wherein additional means are used for modification of the selected tooth replacement parts in the virtual representation in the surrounding area.

7. The system according to claim 5, wherein additional means are used for modification of the set-up of the selected tooth replacement parts in the virtual representation in the surrounding area.

8. The system, according to claim 5, wherein the means for modification of the selected tooth replacement parts comprises a CAD system.

9. The method of claim 1, wherein the tooth replacement parts comprise one or more of crowns, bridges, partial tooth prostheses and total tooth prostheses.

10. The system of claim 5, wherein the tooth replacement parts comprise one or more of crowns, bridges, partial tooth prostheses and total tooth prostheses.

11. The method of claim 1, wherein the tooth replacement parts are adapted to replace at least a portion of one or more of the patient's teeth.

12. The system of claim 5, wherein the tooth replacement parts are adapted to replace at least a portion of one or more of the patient's teeth.

* * * * *